United States Patent

Eiermann et al.

(10) Patent No.: US 6,207,025 B1
(45) Date of Patent: Mar. 27, 2001

(54) PREPARATION OF METHANE SULFONIC ACID

(75) Inventors: Matthias Eiermann, Limburgerhof; Thomas Papkalla, Mannheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/269,759

(22) PCT Filed: Oct. 8, 1997

(86) PCT No.: PCT/EP97/05536

§ 371 Date: Apr. 8, 1999

§ 102(e) Date: Apr. 8, 1999

(87) PCT Pub. No.: WO98/15527

PCT Pub. Date: Apr. 16, 1998

(30) Foreign Application Priority Data

Oct. 9, 1996 (DE) .............................................. 196 41 483

(51) Int. Cl.$^7$ ................................................ C07C 303/00
(52) U.S. Cl. ................................ 204/157.78; 204/157.76
(58) Field of Search ........................... 204/157.76, 157.78

(56) References Cited

U.S. PATENT DOCUMENTS

| | | | |
|---|---|---|---|
| 2,398,479 | * | 4/1946 | Vaughan et al. ................. 204/157.78 |
| 2,702,273 | * | 2/1955 | Kennedy ........................... 204/157.76 |
| 3,050,452 | * | 8/1962 | Louthan ........................... 204/157.76 |
| 3,085,955 | * | 4/1963 | Louthan ........................... 204/157.76 |
| 3,257,302 | * | 6/1966 | Warner ............................. 204/157.76 |
| 3,260,741 | * | 7/1966 | Mackinnon et al. ............. 204/157.78 |
| 3,336,210 | * | 8/1967 | Furrow ............................. 204/157.78 |
| 3,337,437 | * | 8/1967 | Furrow ............................. 204/157.78 |
| 3,392,095 | * | 7/1968 | Dimond ........................... 204/157.78 |
| 3,454,481 | * | 7/1969 | Marrian ........................... 204/157.64 |
| 3,457,155 | * | 7/1969 | Rosinger ......................... 204/157.64 |
| 3,481,849 | * | 12/1969 | Beermann et al. ............. 204/157.64 |
| 4,643,813 | * | 2/1987 | Sato et al. ........................ 204/157.78 |
| 4,997,535 | * | 3/1991 | Tatsumi et al. ................. 204/157.76 |
| 6,042,814 | * | 3/2000 | Koch et al. ............................ 424/60 |

OTHER PUBLICATIONS

K.H. Pfoertner, Ullmann's Encyclopedia of Industrial Chemistry, vol. A 19, pp. 573–586, "Photochemistry", 1991.

Asinger et al., "Die Isomerenbildung bei der photochemischen Sulfochlorierung und Sulfoxydation von Carbonsauren und Carbonsaurederivaten," Tetrahedron Letter, No. 27, 1966, Oxford, GB, pp. 3095–3103, No month available 1966.*

* cited by examiner

Primary Examiner—Kathryn Gorgos
Assistant Examiner—Thao Tran
(74) Attorney, Agent, or Firm—Oblon, Spivak, McClelland, Maier & Neustadt, P.C.

(57) ABSTRACT

A process for preparing methanesulfonic acid by irradiating a mixture comprising acetic acid, sulfur dioxide and oxygen with light, wherein the reaction mixture is irradiated with an average cumulative irradiance in the range from 240 to 320 mm of from 0.05 to 50 mmol quanta/cm$^2$h at the light entry area.

10 Claims, No Drawings

PREPARATION OF METHANE SULFONIC ACID

BACKGROUND OF THE INVENTION

1. Field of the Invention

The present invention relates to an improved process for preparing methanesulfonic acid from a mixture comprising acetic acid, sulfur dioxide and oxygen by irradiation with light.

Methanesulfonic acid is the simplest representative of the class of alkanesulfonic acids and is of great use for a large number of industrial applications such as the production of metal coatings by electrodeposition or else as esterification catalyst.

2. Description of the Related Art

The most widely used processes for preparing methanesulfonic acid are the oxidation of methyl mercaptan or dimethyl disulfide with oxygen or with chlorine to give methanesulfonyl chloride, followed by hydrolysis. All these processes are associated with problems of toxicity and odor, because the starting materials are formed from hydrogen sulfide, which problems can be overcome only with great technical complexity.

DE 907 053 describes the irradiation of carboxylic acids in the presence of air and sulfur dioxide. The reaction products are the corresponding β-sulfo carboxylic acids.

By contrast, irradiation of acetic acid at room temperature in the presence of air and sulfur dioxide takes a different course, as described in Tetrahedron Lett. 1966, 3095. In the reaction, methanesulfonic acid and also 60%, based on the methanesulfonic acid formed, of sulfuric acid are obtained. However, an industrial process with formation of such a large amount of by-product is uneconomic.

BRIEF SUMMARY OF THE INVENTION

It is an object of the present invention to provide an economic process which affords methanesulfonic acid in good yield and in which not more than 50%, based on the methanesulfonic acid, of sulfuric acid is formed.

We have found that this object is achieved by a process for preparing methanesulfonic acid by irradiating a mixture comprising acetic acid, sulfur dioxide and oxygen with light, wherein the reaction mixture is irradiated with an average cumulative irradiance in the range from 240 to 320 nm of from 0.05 to 50 mmol quanta/cm$^2$h at the light entry area.

DETAILED DESCRIPTION OF THE INVENTION

The lamps preferably employed are those emitting light in the range from 240 to 320 nm, such as low pressure mercury lamps, preferably high and medium pressure mercury lamps, either pure or doped, which are commercially available and whose radiated power is from 125 watts to 60 kW. Also suitable are excimer lamps, which are preferably used in the wavelength range from 240 to 320 nm in which sulfur dioxide shows strong absorption.

Further suitable light sources are halogen lamps, gas discharge lamps or fluorescent tubes.

The average cumulative irradiance in the range from 240 to 320 nm at the area where the light enters the reaction mixture is not more than 50 mmol quanta/cm$^2$h, preferably not more than 10 mmol quanta/cm$^2$h, and the effectiveness is optimal with irradiances of up to 5 mmol quanta/cm$^2$h. Irradiances below 0.05 mmol quanta/cm$^2$h slow down the reaction. In a preferred embodiment, irradiation is carried out with an irradiance of 0.1 mmol quanta/cm$^2$h or above.

It is easily possible with knowledge of the quanta flux of the lamp, which is usually stated by the manufacturer, to select a reactor with a suitable irradiation area depending on the lamp output and the required amount to be converted.

Thus, a conventional 150 W high pressure mercury lamp has in the wavelength range of 240–320 nm a quanta flux of 0.128 mol quanta/h and a 700 W lamp has one of 0.6 mol quanta/h.

It is generally known to ensure thorough mixing in irradiation reactions, in particular at the zone of entry of the light into the reaction mixture.

Thorough mixing is achieved, for example, by producing turbulent flow near the wall or high velocities near the wall in the liquid. This can be achieved by reactor tubes which are curved in the region of irradiation, for example in the form of a loop or coil, when the reaction gases are bubbled through the liquid. Effective mixing can generally be achieved by passing the reaction gases as a stream of fine gas bubbles through the reaction mixture. This effect can furthermore be achieved or additionally assisted if the liquid in turn is transported through the reactor. It is also advantageous to use a gas back-mixing stirrer (hollow shaft stirrer).

Preferred types of reactor for the process are, for example, tubular reactors, tube bundle reactors, loop reactors or cocurrent packed columns, which are generally known to the skilled worker.

In a particularly preferred embodiment, the reaction mixture is circulated, for example by pumps or by stirrers, as is the case in the loop reactor. The reaction mixture advantageously flows through the reactor with flow rates of from 0.01 m/s to 1 m/s.

In principle, the various types of loop reactors decribed in "Chemische Reaktionstechnik, Lehrbuch der technischen Chemie", Volume 1, Thieme Verlag, Stuttgart, New York 1992, pages 257–262, are suitable. The liquid can moreover be conveyed in an inner or outer circulation.

The process according to the invention can be carried out either continuously or batchwise.

It is is advantageous if the thickness of the layer of liquid to be irradiated is a multiple of the depth of penetration of the relevant radiation. The thickness of the layer of liquid to be irradiated is preferably at least 1 cm, particularly preferably at least 5 cm. It is likewise economically worthwhile, in order to reduce the holdup, if the thickness of the layer of liquid to be irradiated is chosen to be no larger than 150 cm, preferably no larger than 50 cm.

In industrial equipment, the light source is arranged in front of appropriately transparent windows, such as quartz glass, in the reaction vessels or, preferably as lamps immersed centrally or radially in the reaction chambers.

It is moreover perfectly possible to use more than one lamp if a larger amount of substance is to be reacted. It is also possible in principle to arrange a plurality of lamps in one reactor (Ullmann's encyclopedia of industrial Chemistry, Vol A 19, 5th edition, VCH, Weinheim, 1991, pages 573 to 586.)

In an advantageous embodiment, a loop reactor is chosen, in which case the reaction mixture is conveyed past a plurality of lamps in succession. For reasons of space, the lamps are advantageously arranged parallel to one another to result in a coil reactor. It is preferred in this case to use immersion lamps, but it is likewise possible by a suitable arrangement to convey the reaction mixture between the individual lamps. If a coiled reactor tube is used, the lamp is preferably located in the winding axis of the coil.

It is particularly advantageous to use a loop reactor with an immersion lamp arranged concentrically inside, or a tube bundle reactor where the individual tubes are arranged in the form of a circle around a light source, and the reaction mixture flows through each of them alternatively in parallel or in series. In the latter case, it is advantageous to design the individual tubes in the tube bundle to be flattened toward the light source in order to minimize radiation losses through diffraction or reflection.

To improve utilization of the radiation emitted by the radiation source, or else to promote or inhibit individual steps in the reactions taking place in the reaction mixture, and thus finally to increase the yield, it is possible to add auxiliaries to the reaction mixture.

In a preferred embodiment, sensitizers or photoinitiators are added to the mixture as auxiliaries which permit long wavelength radiation to be used exclusively or additionally. Examples of conventional photoinitiators are:

thermal initiator systems such as hydrogen peroxide, peroxides or azoisobutyronitrile, ketones such as acetophenone, benzophenone or benzanthrone, acyloins such as benzoin derivatives, α-diketones such as diacetyl, phenanthrenequinone or benzil, quinones such as anthraquinone derivatives, sulfur compounds such as diphenyl disulfide or tetramethylthiuram disulfide, halogen compounds such as chlorine, bromotrichloromethane, bromoform or styrene dibromide, metal carbonyls and perchloro compounds such as manganese carbonyl and organic halogen compounds, and hexaarylbisimidazole, fatty acid iodine salts, α-diketone monooxime esters, triphenylphosphine, organic sulfinic acids and dyes, bis(arylsulfonyl)diazomethane, Bunte salts or uranyl salts.

Further preferred auxiliaries are nitrogen oxides, chloroform and the hydroxides and the inorganic or organic salts of copper or cobalt, such as copper or cobalt hydroxide, copper or cobalt sulfate, copper or cobalt sulfite, copper or cobalt carbonate, copper or cobalt bicarbonate, copper or cobalt methanesulfonate or, preferably, copper or cobalt acetate.

The auxiliaries are, as a rule, employed in a concentration of from $10^{-2}$ to 10% by weight, preferbly $10^{-1}$ to 5% by weight, in each case based on acetic acid.

Acetic acid in purities available industrially is suitable for the reaction.

The reaction of acetic acid with sulfur dioxide and oxygen in the presence of light is carried out by ensuring that the mixing of the gases with the acetic acid is as homogeneous as possible. Thus, fine dispersion of the reaction gases can be brought about by known measures, eg. by introduction through nozzles.

The ratio of sulfur dioxide to oxygen may moreover vary. As a rule, equimolar amounts of the gases are passed through the reaction mixture. However, an up to 10 molar excess of one of the gases is also possible. In general, it is advantageous to use acetic acid which is approximately saturated with gas in the temperature range according to the invention.

In a preferred embodiment, 0.01 to 10 mol of sulfur dioxide per mole of acetic acid are passed in continuously during the irradiation period. The same applies to the oxygen. The two gases can be introduced as mixture or separately.

Sulfur dioxide can moreover be fed into the reaction in pure form, liquid or gaseous, or as solution in acetic acid or a suitable solvent, such as water.

It is possible to add sulfur dioxide in the gas mixture with oxygen or an oxygen-containing gas mixture, such as air, to the reaction. The use of a sulfur dioxide/air mixture results in lower partial pressures of the sulfur dioxide and of the oxygen, but this has no detectable effect on the process according to the invention because, as a rule, acetic acid, sulfur dioxide and oxygen are present in excess relative to the effective amount of radiation.

Sulfur dioxide and oxygen or sulfur dioxide and air are preferably passed in together.

To disperse the gases or the gas mixture in the liquid, it is possible to use conventional distributors such as sintered disks, perforated plates, sieve trays and nozzles, preferably glass frits or annular nozzles.

Gas separation takes place in a conventional way after the gas has passed through the irradiation zone.

The process according to the invention is substantially independent of pressure. Elevated pressure can be used, for example up to 20 bar, preferably up to 15 bar. It is likewise possible to choose a slight reduction in pressure down to, for example, 500 mbar. A reduction in pressure diminishes the concentration of sulfur dioxide dissolved in the acetic acid, so that an $SO_2$ concentration which is too low reduces the conversion. The pressure range from 1 to 10 bar is particularly preferred.

The process according to the invention can advantageously be carried out above 0° C., preferably 20° C., in particular 50° C. Side reactions predominate above 160° C., so that the irradiation is preferably carried out at up to 140° C., particularly preferably up to 120° C. The temperature of the mixture can be for example, as generally known, controlled using a jacket on the light source side and a UV-transparent medium such as water.

The reaction can be carried out in inert diluents, where "inert" includes the fact that the diluent has negligible intrinsic absorption in the wavelength range used.

However, the reaction is preferably carried out without diluent.

The irradiation time depends on the amount of acetic acid used, the temperature, pressure and the radiated power of the lamps. For example, 1 l of reaction solution is irradiated with a 150 watt high pressure mercury lamp with a light emission of 0.128 mol quanta/h cumulatively from 240 to 320 mm for from 15 minutes to 20 hours, preferably from 1 to 10 hours.

It may, because of by-product formation, be advantageous to continue the reaction only as far as partial conversion. The reaction is preferably carried out until the methanesulfonic acid content in the total discharge is 20% by weight, in particular 15% by weight.

The product is isolated in a conventional way, as a rule by distillation. It is preferred for acetic acid to be distilled out in a first distillation stage and for the methanesulfonic acid to be distilled out from the bottom product in a second stage. The distillations can in each case be carried out batchwise or continuously, preferably both continuously. The distillations can be carried out under pressures from 0.01 mbar to 1 bar, preferably between 0.1 and 100 mbar. The acetic acid removed in this way if reaction is incomplete, possibly mixed with traces of methanesulfonic acid and/or sulfuric acid, can be reused in this form. Furthermore, the workup is preferably designed so that the sulfuric acid byproduct can be utilized in sulfuric acid cleavage plants.

The process according to the invention can be carried out, for example, by irradiating the acetic acid in a coiled quartz glass tube reactor with, located in the winding axis of the coiled tube, a high pressure mercury lamp. The start and end of the coiled tube are connected by an outside line so that the reaction mixture is circulated by a pump. The two gases are continuously passed in, flowing in the same direction as the liquid.

In a preferred embodiment, a tubular reactor with a high pressure mercury immersion lamp is chosen in place of the coiled tube reactor, with an otherwise identical arrangement. The following examples are intended to illustrate the process according to the invention in detail.

The process according to the invention provides a good yield and a high content of methanesulfonic acid product and thus good selectivity.

EXAMPLE 1

Apparatus

A coiled quartz glass tube with an internal diameter of 1 cm and a tube length of 1.6 m and and internal diameter of the coil of 7 cm has its ends connected by an outside line with incorporated pump. A 150 watt high pressure mercury lamp is located in the winding axis of the coiled tube. 300 g of acetic acid were circulated in this reactor at an ascending flow rate of 80 l/h. At the inlet to the coiled tube, 10 standard-condition liters of air/h and 10 standard-condition liters of sulfur dioxide/h were continuously passed in together and removed downstream of the outlet through a gas/liquid separator. The reaction mixture was irradiated at 90° C. for 6.5 h and then worked up by distillation. Analysis was by quantitative ion chromatography.

Table 1 below summarizes the reaction conditions and results of the tests in Example 1 and in Examples 2 to 4 which were carried out similarly.

TABLE 1

Reaction conditions and results of the photochemical preparation of methanesulfonic acid in a coiled tube reactor

| Ex. | T [° C.] | Acetic acid [g] | Addition to reaction [% by weight] | MSA [g] | $H_2SO_4$/ MSA ratio by weight | Rate [MSA g/kWh] |
|---|---|---|---|---|---|---|
| 1 | 90 | 300 | — | 20.8 | 35/100 | 15 |
| 2 | 90 | 330 | 0.1% $Cu(OCOCH_3)_2$ | 13.9 | 23/100 | 14 |
| 3 | 90 | 314 | 5% $CHCl_3$ | 20.6 | 31/100 | 21 |

MSA = Methanesulfonic acid.

A test carried out as in Example 1 at 60° C. with 330 g of acetic acid as starting compound afforded 18.4 g of methanesulfonic acid. Furthermore, irradiation as in Example 1 at 30° C. afforded 14.0 g of methanesulfonic acid.

EXAMPLE 4 (COMPARATIVE)

100 g of acetic acid in a cylindrical flask (height 14 cm, diameter 4.5 cm) made of quartz glass, besides which was located a 150 Watt high pressure mercury lamp with a quartz cooling jacket at a distance of 5 cm, were irradiated while stirring with a magnetic stirrer at 90° C. for 6.5 h. The complete system was surrounded by a reflecting foil in order to prevent losses of light. During the irradiation, a mixture of sulfur dioxide and air (10 l(STP)/h $SO_2$, 10 l(STP)/h air) was passed in continuously. Working up took place as described above.

The discharge comprised 6 g with a content of 31% by weight MSA = 1.86 g MSA ≙ 1.9 g/kWh MSA.

EXAMPLE 5

In a vertically arranged tubular pressure reactor (length 18 cm, internal diameter 8 cm) with pressure-resistant quartz glass tube (external diameter 4 cm, wall thickness 5 mm) which is concentrically arranged therein and which is connected to both the upper and lower lids pressure-tight in such a way that a light source can be introduced through an appropriate hole in the lid into the interior of the tube, acetic acid and, a concentrically arranged annular nozzle, a gas mixture of sulfur dioxide (40 l (STP)/h) and air (100 l (STP)/h) are passed co-currently upward under pressure. The mixture leaving the reactor is decompressed, and the liquid components are recycled. 1100 g of acetic acid were circulated in this reactor, being pumped upward at a flow rate of 80 to 100 l/h. The reaction mixture was irradiated with a 150 W high-pressure mercury vapor lamp at 90° C. under 4 bar for 6.5 h. 39 g of methanesulfonic acid (40 g/kWh) were obtained, with a ratio of sulfuric acid to methanesulfonic acid of 50/100 by weight.

EXAMPLES 6 to 8

In a vertically arranged tubular reactor (length 25 cm, internal diameter 15 cm) with quartz glass tube (external diameter 6 cm) which is concentrically arranged therein and which is connected to the upper lid in such a way that a high-pressure mercury vapor lamp can be introduced through an appropriate opening in the lid into the interior of the tube, acetic acid and, through a glass annular nozzle or frit arranged in the middle of the base of the reactor, sulfur dioxide and a nitrogen/oxygen mixture are passed co-currently upward. The liquid components of the discharge from the reactor are recycled. 4200 g of acetic acid were circulated in this reactor, being pumped upward at a flow rate of 80 l/h at 90° C. The reaction mixture was irradiated with high-pressure mercury vapor lamps at 90° C. under atmospheric pressure for 6.5 h.

Quanta fluxes of the lamps (240 to 320 nm)=The 150 W lamp has a quanta flux of 0.128 mol quanta/h. The 700 W lamp has a quanta flux of 0.6 mol quanta/h.

TABLE 2

Reaction conditions and experimental results for Examples 6 to 9

| Ex. | Gas introduction | $SO_2$ [L(STP)/h] | $N_2/O_2$ | Lamp | MSA [g] | $H_2SO_4$/MSA ratio by weight | MSA rates [g/kWh] |
|---|---|---|---|---|---|---|---|
| 6 | Annular nozzle | 40 | 8/2, 40 l(STP)/h | 150 W | 48 | 39/100 | 71 |
| 7 | Glass frit | 20 | 8/2, 20 l(STP)/h | 700 W | 199 | 8.5/100 | 44 |

TABLE 2-continued

Reaction conditions and experimental results for Examples 6 to 9

| Ex. | Gas introduction | SO$_2$ [L(STP)/h] | N$_2$/O$_2$ | Lamp | MSA [g] | H$_2$SO$_4$/MSA ratio by weight | MSA rates [g/kWh] |
|---|---|---|---|---|---|---|---|
| 8 | Glass frit | 40 | 8/2, 160l(STP)/h | 700 W | 399 | 23/100 | 88 |

What is claimed is:

1. A process for preparing methanesulfonic acid by irradiating a mixture comprising acetic acid, sulfur dioxide and oxygen, wherein the cumulative irradiance in the range from 240 to 320 nm averages from 0.1 to 50 mmol quanta/cm$^2$h at the area where the light enters the reaction mixture.

2. A process as claimed in claim 1, wherein the reaction is carried out in a loop reactor.

3. A process as claimed in claim 1, wherein the radiation source is a lamp immersed in the reaction mixture.

4. A process as claimed in claim 1, wherein auxiliaries are added to the reaction mixture.

5. A process as claimed in claim 1, wherein the reaction is carried out under an absolute pressure of up to 20 bar.

6. A process as claimed in claim 1 where the cumulative irradiance where the light enters the reaction mixture is not more than 10 mmol quanta/cm$^2$h.

7. A process as claimed in claim 1 wherein the reaction is carried out at from 0 to 160° C.

8. A process as claimed in claim 7, wherein the radiation source is a lamp immersed in the reaction mixture.

9. A process as claimed in claim 7, wherein auxiliaries are added to the reaction mixture.

10. A process as claimed in claim 7, wherein the reaction is carried out under an absolute pressure of up to 20 bar.

* * * * *